(12) United States Patent
Yao et al.

(10) Patent No.: US 9,259,199 B2
(45) Date of Patent: Feb. 16, 2016

(54) IMAGE PROCESSING APPARATUS AND X-RAY DIAGNOSIS APPARATUS

(75) Inventors: Jingwu Yao, Buffalo Grove, IL (US); Takuya Sakaguchi, Shioya-gun (JP)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 443 days.

(21) Appl. No.: 13/117,578

(22) Filed: May 27, 2011

(65) Prior Publication Data

US 2012/0300903 A1     Nov. 29, 2012

(51) Int. Cl.
*A61B 6/00* (2006.01)
*A61B 6/12* (2006.01)
*G06T 7/00* (2006.01)

(52) U.S. Cl.
CPC . *A61B 6/481* (2013.01); *A61B 6/12* (2013.01); *A61B 6/487* (2013.01); *A61B 6/504* (2013.01); *A61B 6/507* (2013.01); *A61B 6/5217* (2013.01); *G06T 7/0016* (2013.01); *G06T 2207/10121* (2013.01); *G06T 2207/20044* (2013.01); *G06T 2207/20148* (2013.01); *G06T 2207/30021* (2013.01); *G06T 2207/30101* (2013.01)

(58) Field of Classification Search
CPC .................. A61B 6/504; A61B 6/5217; G06T 2207/20044; G06T 2207/20148; G06T 2207/30021; G06T 2207/30101
See application file for complete search history.

(56) References Cited

U.S. PATENT DOCUMENTS

| 7,496,175 | B2 | 2/2009 | Sakaguchi et al. | |
|---|---|---|---|---|
| 2003/0069499 | A1 | 4/2003 | Lienard et al. | |
| 2007/0195932 | A1 | 8/2007 | Nakaura et al. | |
| 2008/0107233 | A1* | 5/2008 | Sakaguchi et al. | 378/91 |
| 2008/0281205 | A1* | 11/2008 | Naghavi et al. | 600/458 |
| 2009/0310847 | A1* | 12/2009 | Matsuzaki | A61B 6/504 382/132 |
| 2010/0002828 | A1 | 1/2010 | Miura | |
| 2010/0172556 | A1* | 7/2010 | Cohen et al. | 382/128 |

(Continued)

FOREIGN PATENT DOCUMENTS

| CN | 101023871 A | 8/2007 |
|---|---|---|
| CN | 101176669 A | 5/2008 |

(Continued)

OTHER PUBLICATIONS

Chinese Office Action with its English translation for Chinese Patent Application No. 201210167330.0 mailed on Mar. 26, 2014.

(Continued)

*Primary Examiner* — Vu Le
*Assistant Examiner* — Kenny Cese
(74) *Attorney, Agent, or Firm* — Yoshida & Associates, LLC

(57) ABSTRACT

According to one embodiment, an image processing apparatus includes a storage unit, a specifying unit, an extraction unit and a setting processing unit. The storage unit stores first X-ray image data in which a blood vessel of an object is not visually enhanced, and second X-ray image data in which the blood vessel is visually enhanced. The specifying unit specifies a catheter image included in the first fluoroscopic image by performing image processing of the first X-ray image data. The extraction unit extracts a blood vessel region included in the second fluoroscopic image by performing image processing of the second X-ray image data. The setting processing unit sets a region of interest based on the position of end point of the catheter.

10 Claims, 6 Drawing Sheets

(56) References Cited

U.S. PATENT DOCUMENTS

| | | | |
|---|---|---|---|
| 2010/0183207 A1* | 7/2010 | Sakaguchi | A61B 6/507 382/128 |
| 2010/0278410 A1* | 11/2010 | Ohishi | 382/131 |
| 2012/0155737 A1* | 6/2012 | Sakaguchi et al. | 382/132 |
| 2013/0012813 A1 | 1/2013 | Sakaguchi | |

FOREIGN PATENT DOCUMENTS

| | | |
|---|---|---|
| CN | 101484073 A | 7/2009 |
| CN | 101677799 A | 3/2010 |
| CN | 101785679 A | 7/2010 |
| CN | 101856239 A | 10/2010 |
| CN | 102958440 A | 3/2013 |
| JP | 2005-261473 A | 9/2005 |
| JP | 2010-246725 A | 11/2010 |

OTHER PUBLICATIONS

Japanese Office Action with its English Summary for the corresponding Japanese Patent Application No. 2012-096445 mailed on Dec. 8, 2015.

* cited by examiner

Right coronary artery
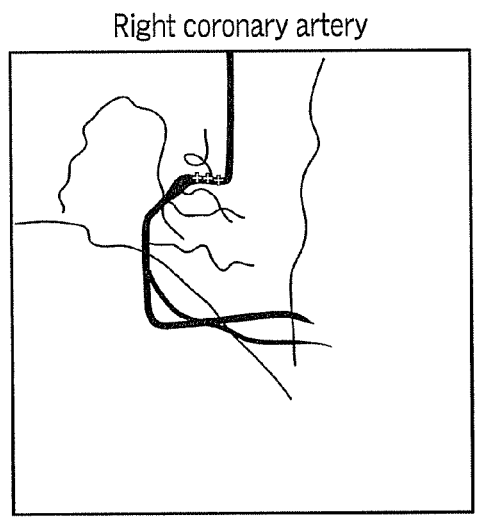
F I G. 4A
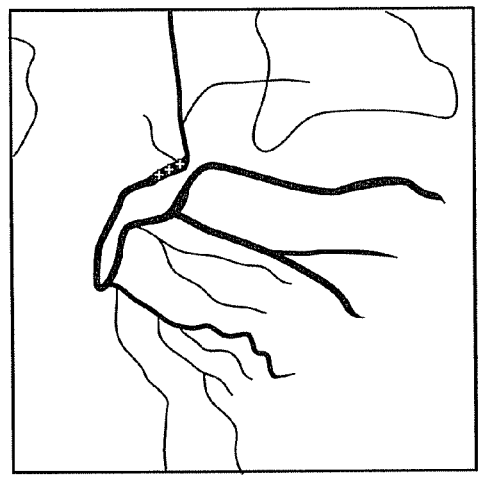
F I G. 4B
Left coronary artery
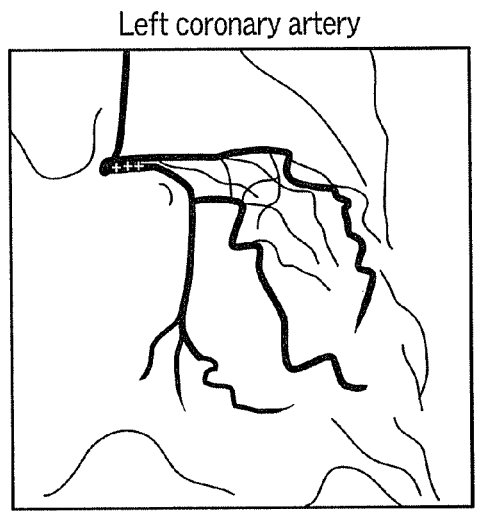
F I G. 4C
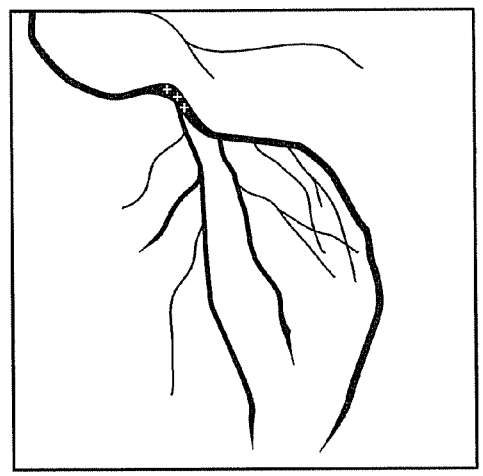
F I G. 4D
"Spider" view of arteries
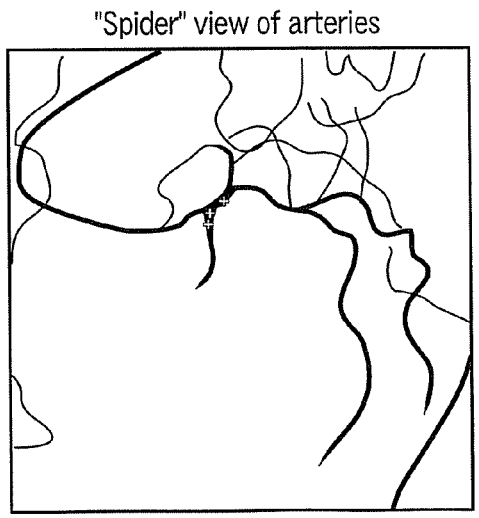
F I G. 4E

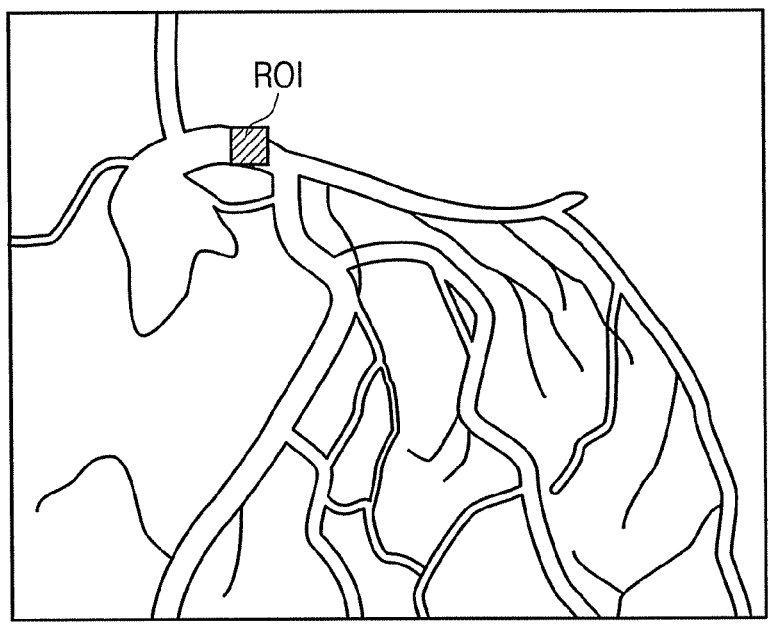
F I G. 6
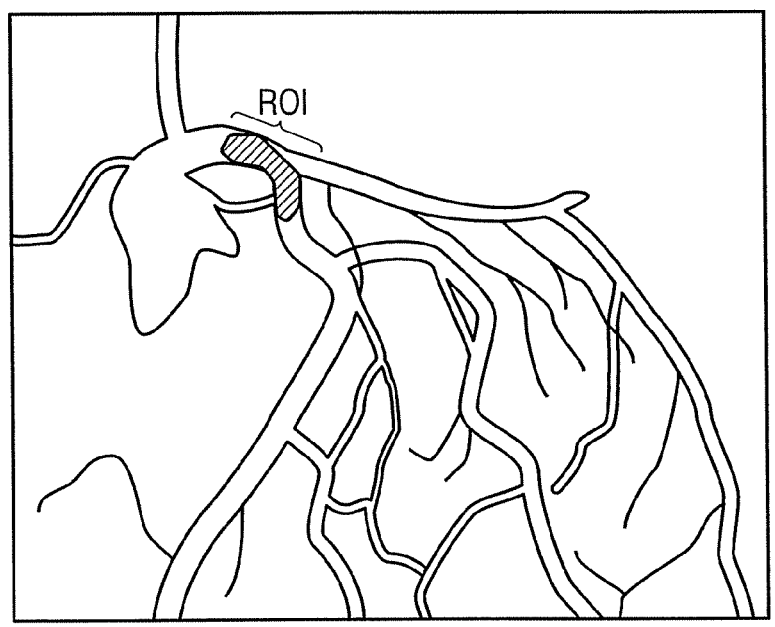
F I G. 7

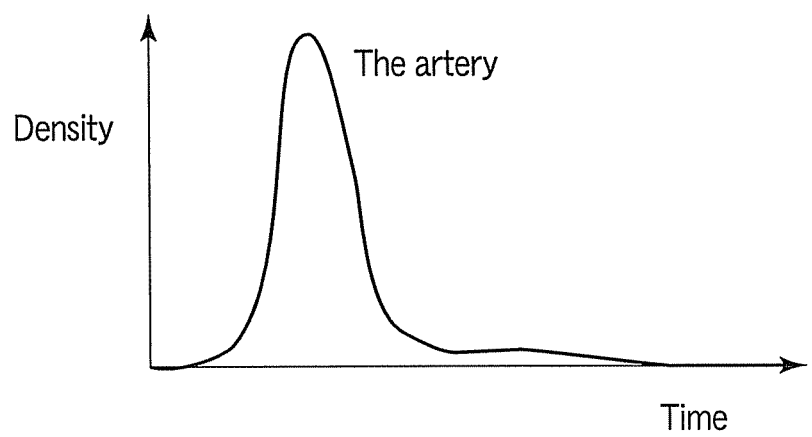
F I G. 8

IMAGE PROCESSING APPARATUS AND X-RAY DIAGNOSIS APPARATUS

FIELD

Embodiments described herein relate generally to an image processing apparatus and an X-ray diagnosis apparatus.

BACKGROUND

X-ray image processing apparatuses for cardiovascular disease have been developed as image guide apparatuses used for angiographic examination and interventional treatment which examines and treats arteries and veins in the whole body. X-ray image processing apparatuses process images obtained by X-ray imaging in the state where a contrast medium is injected in blood vessels, and display image data on an image display unit or apparatus.

In, for example, coronary angiography, a contrast medium is injected through a catheter inserted at the proximal of a coronary artery. Arterial examination measures the degree of stain of a blood vessel, and tissue examination measures the degree of stain of myocardial tissue. In the latter examination, there is known a method for measuring the flow in myocardial tissue, namely, perfusion, on the basis of the degree of stain.

In these types of measurement, it is necessary to set a region of interest (ROI) on an image and acquire time-density information relating to the ROI. In a conventional method for determining a ROI, the operator has to operate the mouse or buttons of a computer by means of the Graphical User Interface (GUI) or the like, while simultaneously observing an X-ray image. However, the operation may be troublesome to perform, and the operation performed may vary depending upon the skill of the operator. In addition, it is not desirable to perform the operation in a clean room such as a room where intravascular treatment is being performed. There have been needs to automate ROI setting, and hence demands have arisen for some technical developments.

BRIEF DESCRIPTION OF THE DRAWINGS

FIGS. 4A, 4B, 4C, 4D and 4E are exemplary views each showing an example of the image displayed on a display unit 11;

FIG. 6 is a view showing an example of a ROI set on the coronary angiogram according to an embodiment;

FIG. 7 is view showing an example of a ROI set on the coronary angiogram according to an embodiment; and FIG. 8 is a graph showing an example of a time-density curve displayed on a user interface.

DETAILED DESCRIPTION

In general, according to one embodiment, an image processing apparatus includes a storage unit, a specifying unit, an extraction unit and a setting processing unit. The storage unit stores first X-ray image data in which a blood vessel of an object is not visually enhanced, and second X-ray image data in which the blood vessel is visually enhanced. The specifying unit specifies a catheter image included in the first fluoroscopic image by performing image processing of the first X-ray image data. The extraction unit extracts a blood vessel region included in the second fluoroscopic image by performing image processing of the second X-ray image data. The setting processing unit sets a region of interest based on the position of end point of the catheter.

Figure 1:
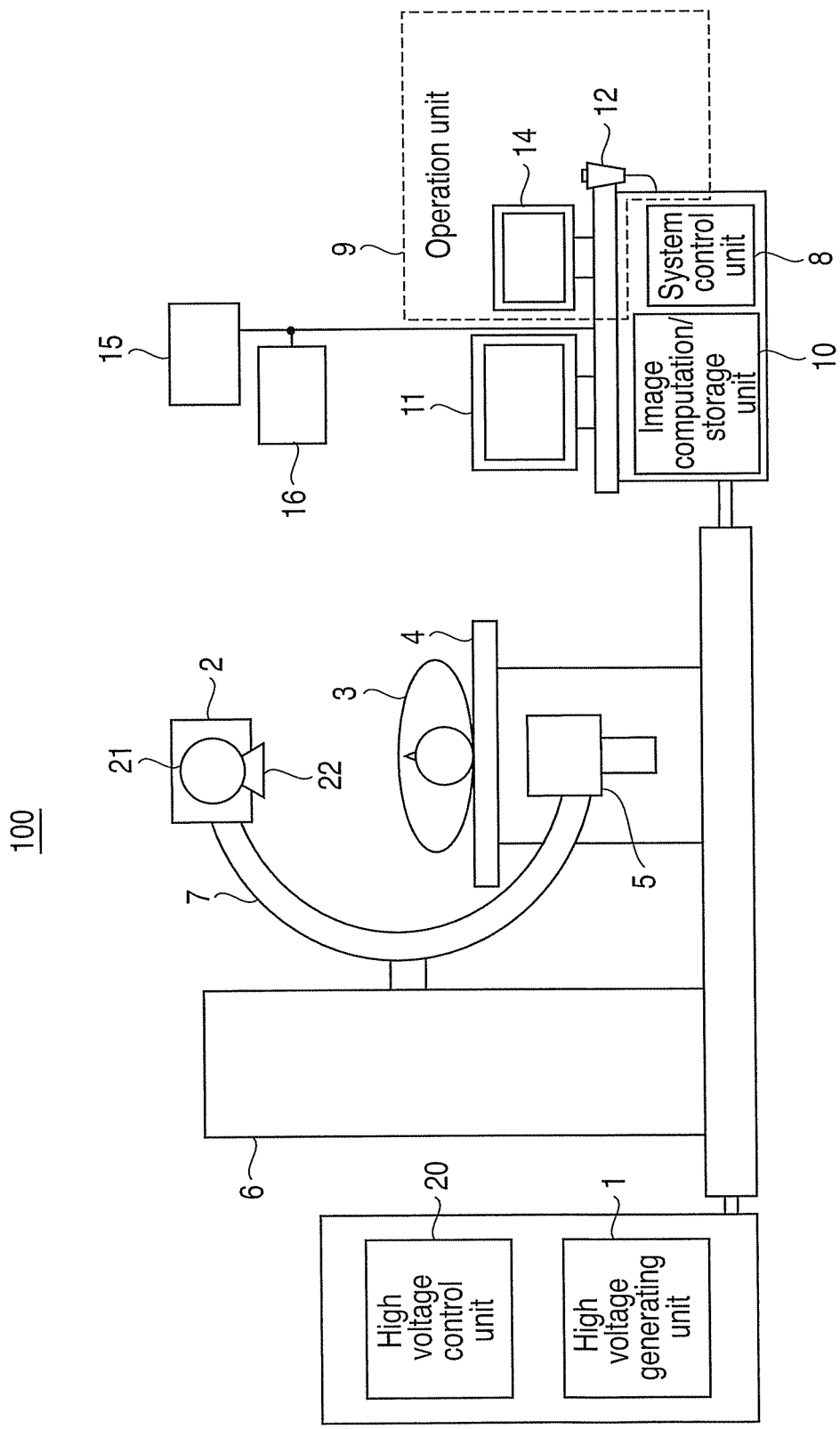
FIG. 1 is an exemplary view showing the arrangement of an X-ray diagnosis apparatus according to an embodiment.

FIG. 1 shows an exemplary view showing the arrangement of an X-ray diagnosis apparatus according to this embodiment. The X-ray diagnosis apparatus includes a gantry 100. The gantry 100 includes a C-arm 7. The C-arm 7 is rotatably supported on a support mechanism 6. An X-ray generating unit 2 is mounted on one end of the C-arm 7. The X-ray generating unit 2 includes an X-ray tube 21 and an X-ray collimator 22. A high voltage generating unit 1 generates a high voltage (tube voltage) to be applied between the electrodes of the X-ray collimator 22. The high voltage generating unit 1 also generates a filament current to be supplied to the filament of the X-ray collimator 22. A high voltage control unit 20 controls the tube voltage and/or filament current generated by the high voltage generating unit 1 under the control of a system control unit 8.

An X-ray detection unit 5 is mounted on the other end of the C-arm 7. The X-ray detection unit 5 faces the X-ray collimator 22 of the X-ray generating unit 2 through an object 3 placed on a bed 4. The X-ray detection unit 5 is typically a solid-state flat panel detector constituted by a two-dimensional array of a plurality of detection elements (pixels) to directly or indirectly convert incident X-rays into electric charge. Typically, the X-ray detection unit 5 periodically repeats detection operation, under the control of the system control unit 8, in which one cycle includes storing electric charge, reading electric charge, and resetting electric charge.

The system control unit 8 has a main function of controlling imaging operation based on an injection start signal to be output from an injector 15 at the instant when the injector 15 starts injecting a contrast medium into the object 3, an injection end signal to be output from the injector 15 at the instant when the injector 15 finishes injecting the contrast medium into the object, and an electrocardiogram (ECG) of the object 3 measured by an electrocardiograph 16.

An image computation/storage unit 10 has a function of generating image data based on an output from the X-ray detection unit 5, a function of storing the image data, and a function of processing the image data. That is, the image computation/storage unit 10 acquires and stores X-ray image data before and after the injection of a contrast medium. The image computation/storage unit 10 has a function of extracting a blood vessel region and catheter image of the object which are included in the stored X-ray image data and performing thinning processing. The image computation/storage unit 10 has a function of calculating the positional relationship between an end point of the catheter (catheter tip) and the center line of the blood vessel region from the respective data of the thinned blood vessel region and catheter image. The image computation/storage unit 10 also has a function of setting, as an ROI, a position separated from the end point of the catheter by a predetermined distance along the center line of the blood vessel region, based on this positional relationship.

An operation unit 9 is connected to the system control unit 8. The operation unit 9 is provided with a hand switch 12 and a user interface 14 including a display and a touch panel.

Figure 2:
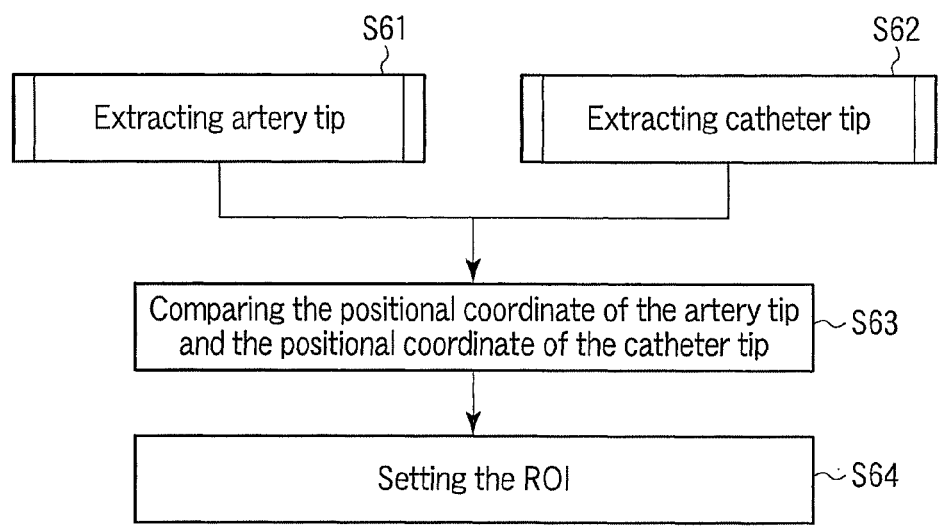
FIG. 2 is a flowchart showing a basic processing procedure by the X-ray diagnosis apparatus according to an embodiment.

FIG. 2 is a flowchart showing a basic processing procedure by the X-ray diagnosis apparatus having the above arrangement. As shown in the flowchart, the image computation/storage unit 10 performs image processing to extract an end point of an artery and the catheter tip (steps S61 and S62). In other words, the position coordinates of the end point of the artery and the position coordinates of the catheter tip are extracted.

Next, the image computation/storage unit 10 compares the position coordinates of the end point of the artery with those of the catheter tip, and finds a region where the end point of the artery and the catheter tip are close to each other (step S63). Then, the image computation/storage unit 10 sets a ROI in which the artery is located away from the catheter tip by a predetermined distance (step S64).

Figure 3:
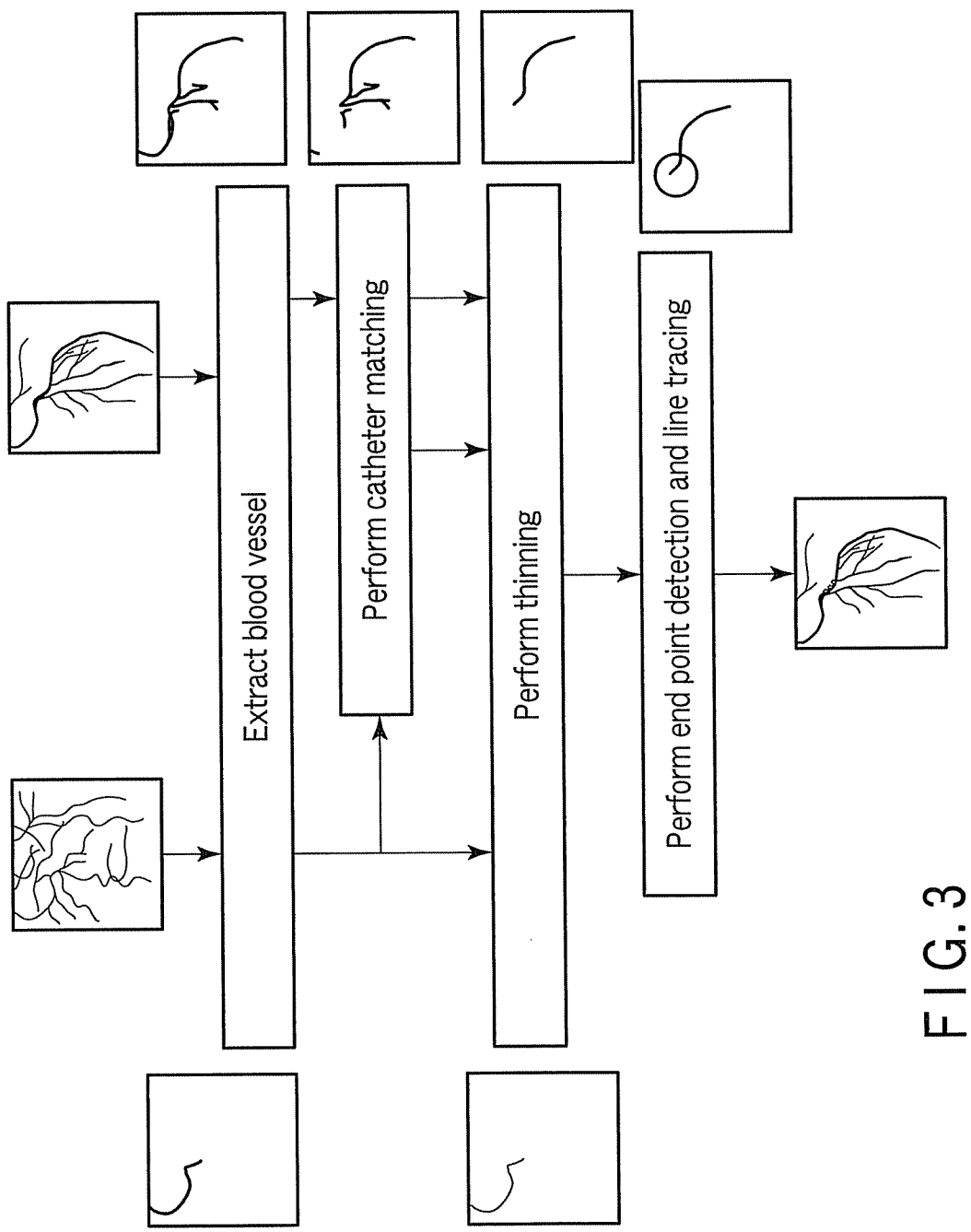
FIG. 3 is a flowchart showing a more detailed processing procedure by the X-ray diagnosis apparatus according to an embodiment.

FIG. 3 is a flowchart showing a more detailed processing procedure by the X-ray diagnosis apparatus shown in FIG. 1. In step ST1 in FIG. 3, the image computation/storage unit 10 reads out a contrast-non-enhanced frame 2a and a contrast-enhanced frame 2b which are stored in advance. A catheter image is extracted from the contrast-non-enhanced frame 2a. Binary image data represented by, for example, 2c is extracted. In addition to a catheter image, a blood vessel region is extracted from the contrast-enhanced frame 2b. With this operation, binary image data represented by, for example, 2d is extracted.

In other words, according to the embodiment, image processing is carried out by use of the frame 2a in which the blood vessel of the object is not visually enhanced and the frame 2b in which the blood vessel is visually enhanced. An image of the catheter is included in both the two frames 2a and 2b.

Next, the image computation/storage unit 10 extracts the catheter region from the image data 2c and 2d in step ST2. To be more specific, the image computation/storage unit 10 uses image data 2c as a template, and compares it with image data 2d. Based on the binary value comparison between pixels of the data, a degree of correlation is evaluated with reference to the template. Based on this evaluation, a catheter region included in the image data is extracted. This process is referred to as catheter matching. By this processing, the catheter portion and the blood vessel portion are individually specified in the image.

In step ST3, the image computation/storage unit 10 further performs thinning processing for the image data of the specified blood vessel region and catheter region, thereby calculating the center lines of the blood vessel and catheter. The image computation/storage unit 10 obtains an image represented by, for example, 2f from the catheter image. The image computation/storage unit 10 obtains an image represented by, for example, 2g by thinning processing of the blood vessel region.

In step ST4, the image computation/storage unit 10 further detects the positional coordinates of the end point (tip) of the catheter. In general, the catheter tip is detected as two positions. In the embodiment, the end pointed closer to the center of an image is selected for processing.

Next, the image computation/storage unit 10 performs line tracing. If a branch of a blood vessel is detected in the line tracing, the image computation/storage unit 10 traces each branch of the blood vessel, detects a region where the branch width is large enough (e.g., larger than 1 mm), and sets that region as a ROI candidate.

Further, the line tracing is processing wherein line segments included in an image and branch points of the line segments are detected. In the processing, a combination of bit patterns that is defined as a small region (e.g. 3×3 pixels) is compared with all pixel values ("0" or "1") constituting a binary image, and the bit patterns identical to small regions of the image are detected. From the bit pattern distribution obtained for each adjacent pair of small regions, the shapes of the line segments included in the image are recognized. The image computation/storage unit 10 performs this processing for the center line of a thin-blood-vessel region.

The image computation/storage unit 10 sets an ROI at a position on a center line of the blood vessel which is spaced apart from the tip of the catheter by a predetermined distance (e.g., about 2 mm to 5 mm) using the result obtained by line tracing processing. In this manner, the positional coordinates of the ROI center are automatically detected. Assume that an ROI is set at a position represented by, for example, 2h. In this case, the system control unit 8 displays an image on the display unit 11 with a symbol corresponding to the ROI being superimposed on the contrast-enhanced frame 2b.

FIGS. 4A to 4E each show an example of the image displayed on the display unit 11. FIGS. 4A and 4B each show a state in which symbols (crosses) indicating the center positions of ROIs are superimposed and displayed on an X-ray image of the right coronary artery. FIGS. 4C and 4D each show a state in which symbols (crosses) indicating ROIs are superimposed and displayed on an X-ray image of the left coronary artery. FIG. 4E shows a state in which ROI symbols (crosses) are superimposed and displayed on a "spider" view of arteries. In the above manner, according to this embodiment, ROIs are automatically superimposed and displayed on various kinds of X-ray fluoroscopic images.

Figure 5:
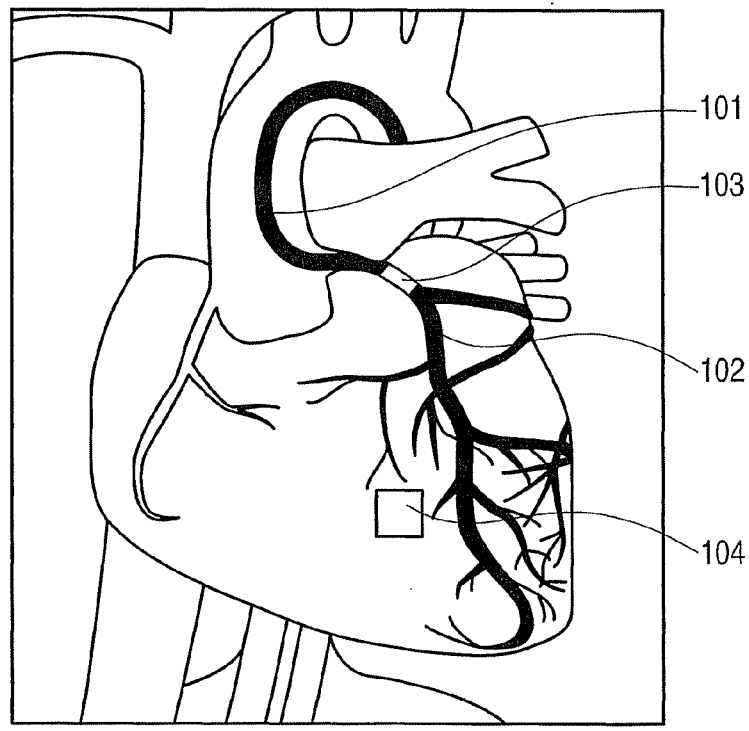
FIG. 5 is a view showing an example of a coronary angiogram according to an embodiment.

FIG. 5 shows an example of a coronary angiogram (hereinafter referred to as an "CAG image") obtained in general X-ray angiophotography. The CAG image is featured in that the amount of X-ray absorbed in the contrast medium is large. When the contrast medium passing through the coronary artery, the shape of the coronary artery can be observed with a sufficiently high contrast that enables discrimination between the coronary artery and other kinds of tissue.

As shown in FIG. 5, the catheter 101 is inserted into the coronary artery 102, and the contrast medium is injected continuously into the coronary artery for a predetermined period of time. X-ray imaging is performed during a period starting from a time which is immediately before the injection of the contrast medium to a time which is a predetermined time after the end of the injection of the contrast medium.

When the contrast medium is injected into the coronary artery through the catheter 101, the X-ray diagnosis apparatus shown in FIG. 1 collects X-ray images. At the end of the image collection, a ROI is automatically determined by computation, and a reference region 103 of ROI on the coronary artery (the reference region 103 is a myocardial blood supply region) and a plurality of myocardial local regions 104 on the cardiac muscle are set on a CAG image.

The myocardial local regions 104 are determined on the area of the cardiac muscle and typically include a plurality of pixels. The density in the myocardial local regions 104, which represents the amount of contrast medium perfusion, is typically calculated as a pixel average value. The myocardial local regions 104 may include a single pixel. The myocardial blood supply region 103 is typically a rectangular region whose width is substantially equal to the width of a blood vessel or slightly smaller than the width of the blood vessel. The myocardial blood supply region 103 has its longer axis extend along the blood vessel and contains a plurality of pixels. The density in the myocardial blood supply region 103, which represents the amount of contrast medium injected, is typically calculated as a pixel average value. The myocardial blood supply region 103 is set at an arbitrary position in a flow passage between the injector 15 and a myocardial region of interest, more specifically at an arbitrary position of the catheter, or at an arbitrary position in a flow passage between the outlet port of the injector 15 (which port is equivalent to the inlet port of the coronary artery) and the myocardial region of interest. The ROI set in this manner is displayed on the CAG image, as shown in FIG. 6 or 7. FIG. 6 shows a rectangular region as a ROI, and FIG. 7 shows a polygonal region with a fixed area as a ROI.

The image computation/storage unit 10 generates a time-density curve (TDC) pertaining to the myocardial blood supply region 103. Likewise, the image computation/storage unit 10 generates a plurality of time-density curves pertaining to the myocardial local regions 104.

FIG. 8 is a graph showing an example of a time-density curve displayed on the user interface 14. The time-density curve represents how the density of the contrast medium injected into the coronary artery changes with time. The time-density curve is generated by the image computation/storage unit 10 by computation. A time-to-peak (TTP) value pertaining to the density of the contrast medium may be in the form of a graph. Alternatively, a graph may be prepared using, as an index, blood flow information such as a perfusion volume, a blood volume, or an average passage time of blood. Furthermore, a two-dimensional distribution of index values pertaining to the perfusion in myocardial tissue may be used as perfusion information.

As described above, this embodiment specifies an ROI on a blood vessel on a side close to a catheter, and also specifies a blood vessel center line. That is, processing on the system side can set an ROI without designation by manual operation by the operator. Since this embodiment can automatically detect an ROI, giving software information indicating the detection of an ROI as a trigger can make various types of processing automatically run. In addition, this embodiment can determine many time density curves and select one as a reference curve.

For example, with reference to an ROI on a side close to the catheter, it is possible to measure time density curve information automatically at another ROI on the blood vessel. That is, it is possible to automatically measure, at the other ROI, a time delay and the degree of amplitude decrease compared to of the reference ROI closest to the catheter. It is also possible to display a measurement result image and a blood vessel graph.

As described above, this embodiment uses X-ray image data before and after the injection of a contrast medium to extract a catheter portion from the image data before the injection of the contrast medium and extract a blood vessel portion from the image data after the injection of the contrast medium. The embodiment calculates an end portion of the catheter and the center line of the blood vessel by performing thinning processing for each extracted image data. The embodiment then specifies, as an ROI, coordinates on the blood vessel center line which is separated from the catheter end portion by a predetermined distance. According to the embodiment, therefore, it is possible to automatically set an ROI.

Note that the embodiment is not limited to the above. In relation to the embodiment, reference was made to the case where a ROI is set based on an image showing a contrast medium injected into the coronary artery of the heart. However, this embodiment can be applied to all general angiographic examinations using catheters, e.g., cerebral angiography and abdominal angiography. Automatically setting an ROI can acquire the time density curves of the contrast medium injected in all kinds of blood vessels in the body as well as in the case of heart.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
a storage configured to store first X-ray image data in which a blood vessel of an object is not visually enhanced, and second X-ray image data in which the blood vessel is visually enhanced;
a specifier configured to specify a catheter image of a catheter included in a first fluoroscopic image by performing image processing of the first X-ray image data;
an extractor configured to extract a blood vessel region included in a second fluoroscopic image by performing image processing of the second X-ray image data;
a setting processor configured to set a region of interest based on the position of end point of the catheter;
a display configured to automatically display a symbol corresponding to the region of interest on at least one of the first fluoroscopic image and the second fluoroscopic image;
a thinning processor configured to calculate a positional relationship between an end point of the catheter image and a center line of the blood vessel region by thinning the catheter image and a blood vessel image; and
a calculation processor configured to calculate blood flow information associated with the set region of interest; wherein
the setting processor sets, as a plurality of the regions of interest, from the end point a plurality of positions separated by a predetermined distance along the center line, based on the positional relationship, using a result obtained by line tracing processing,
the calculation processor calculates time density curve information on another region of interest on the blood vessel based upon one regions of interest that is on a closer side to the catheter among the plurality of the regions of interest, and if a branch of a blood vessel is detected in the line tracing processing, the setting processor traces the branch of the blood vessel, detects a region where a branch width of the branch is substantially large and sets the region as a region of interest candidate.

2. The apparatus according to claim 1, wherein the blood flow information indicates a time density curve in a coronary artery.

3. The apparatus according to claim 2, wherein the blood vessel is a coronary artery.

4. The apparatus according to claim 3, wherein the blood flow information comprises a two-dimensional distribution of index values pertaining to perfusion in myocardial tissue.

5. The apparatus according to claim 1, wherein the calculation processor is configured to compute perfusion information with respect to regions, using the set region of interest as a reference.

6. An X-ray diagnosis apparatus comprising:
an X-ray tube configured to generate X-rays;
an X-ray detector configured to detect X-rays generated by the X-ray tube and transmitted through an object;
an image generator configured to generate first X-ray image data in which a blood vessel of the object is not visually enhanced, and second X-ray image data in which the blood vessel is visually enhanced;
a specifier configured to specify a catheter image of a catheter included in a first fluoroscopic image by performing image processing of the first X-ray image data;
an extractor configured to extract a blood vessel region included in a second fluoroscopic image by performing image processing of the second X-ray image data;
a calculation processor configured to calculate blood flow information associated with the set region of interest;
a setting processor configured to set a region of interest based on the position of end point of the catheter;
a display configured to automatically display a symbol corresponding to the region of interest on at least one of the first fluoroscopic image and the second fluoroscopic image; and
a thinning processor configured to calculate a positional relationship between an end point of the catheter image and a center line of the blood vessel region by thinning the catheter image and a blood vessel image, wherein the setting processor sets, as a plurality of the regions of interest, from the end point a plurality of positions separated by a predetermined distance along the center line, based on the positional relationship, using a result obtained by line tracing processing, wherein the calculation processor calculates time density curve information on another region of interest on the blood vessel based upon one of the of the regions of interest that is on a closer side to the catheter among the plurality of the regions of interest, and if a branch of a blood vessel is detected in the line tracing processing, the setting processor traces the branch of the blood vessel, detects a region where a branch width of the branch is substantially large and sets the region as a region of interest candidate.

7. The apparatus according to claim 6, wherein the blood flow information indicates a time density curve in a coronary artery.

8. The apparatus according to claim 7, wherein the blood vessel is a coronary artery.

9. The apparatus according to claim 8, wherein the blood flow information comprises a two-dimensional distribution of index values pertaining to perfusion in myocardial tissue.

10. The apparatus according to claim 6, wherein the calculation processor is configured to compute perfusion information with respect to regions, using the set region of interest as a reference.

* * * * *